(12) United States Patent  (10) Patent No.: US 7,648,462 B2
Jenkins et al. (45) Date of Patent: *Jan. 19, 2010

(54) SAFETY SYSTEMS AND METHODS FOR ENSURING SAFE USE OF INTRA-CARDIAC ULTRASOUND CATHETERS

(75) Inventors: David A. Jenkins, Flanders, NJ (US); Charles Bryan Byrd, Medford, NJ (US); Praveen Dala-Krishna, Bensalem, PA (US)

(73) Assignee: St. Jude Medical, Atrial Fibrillation Division, Inc., St. Paul, MN (US)

(*) Notice: Subject to any disclaimer, the term of this patent is extended or adjusted under 35 U.S.C. 154(b) by 17 days.

This patent is subject to a terminal disclaimer.

(21) Appl. No.: 10/998,039

(22) Filed: Nov. 29, 2004

(65) Prior Publication Data

US 2005/0124899 A1 Jun. 9, 2005

Related U.S. Application Data

(63) Continuation-in-part of application No. 10/345,806, filed on Jan. 16, 2003, now Pat. No. 6,908,434.

(60) Provisional application No. 60/349,060, filed on Jan. 16, 2002.

(51) Int. Cl.
*A61B 8/14* (2006.01)
(52) U.S. Cl. .................................................. 600/466
(58) Field of Classification Search ............... 600/437, 600/459, 466
See application file for complete search history.

(56) References Cited

U.S. PATENT DOCUMENTS

| 3,917,979 | A | 11/1975 | Volk, Jr. |
| 4,161,121 | A | 7/1979 | Zitelli et al. |
| 4,241,610 | A | 12/1980 | Anderson |
| 4,413,633 | A | 11/1983 | Yanda |
| 4,462,408 | A | 7/1984 | Silverstein et al. |
| 4,519,260 | A | 5/1985 | Fu et al. |
| 4,522,194 | A | 6/1985 | Normann |
| 4,576,177 | A | 3/1986 | Webster, Jr. |
| 4,605,009 | A | 8/1986 | Pourcelot et al. |
| 4,841,977 | A | 6/1989 | Griffith et al. |

(Continued)

OTHER PUBLICATIONS

Keith S. Dickerson et al., "Comparison of Conventional and Transverse Doppler Sonograms", J. Ultrasound Med., 1993, pp. 497-506, vol. 12.

(Continued)

*Primary Examiner*—Long V Le
*Assistant Examiner*—Jacqueline Cheng
(74) *Attorney, Agent, or Firm*—The Marbury Law Group, PLLC

(57) ABSTRACT

A system and method for limiting a temperature induced in a body by an ultrasound imaging catheter are provided. The method includes receiving, at an isolation box, an imaging signal from an imaging catheter, receiving, at an isolation box, a signal indicative of a temperature of tissue adjacent to the imaging catheter, removing power to the imaging catheter at the isolation box if the signal indicates the temperature of tissue adjacent to the imaging catheter exceeds a known value, and sending the imaging signal from the catheter to a processor if the signal indicates the temperature of tissue adjacent to the imaging catheter is less than the limit.

14 Claims, 4 Drawing Sheets

U.S. PATENT DOCUMENTS

| | | | |
|---|---|---|---|
| 4,890,268 A | 12/1989 | Smith et al. | |
| 4,917,097 A | 4/1990 | Proudian et al. | |
| 4,951,677 A | 8/1990 | Crowley et al. | |
| 5,002,059 A | 3/1991 | Crowley et al. | |
| 5,090,956 A | 2/1992 | McCoy | |
| 5,152,294 A | 10/1992 | Mochizuki et al. | |
| 5,158,087 A * | 10/1992 | Gatzke | 600/459 |
| 5,170,793 A | 12/1992 | Takano et al. | |
| 5,195,968 A | 3/1993 | Lundquist et al. | |
| 5,254,088 A | 10/1993 | Lundquist et al. | |
| 5,279,559 A | 1/1994 | Barr | |
| 5,304,214 A | 4/1994 | DeFord et al. | |
| 5,307,816 A | 5/1994 | Hashimoto et al. | |
| 5,309,914 A | 5/1994 | Iinuma | |
| 5,325,860 A | 7/1994 | Seward et al. | |
| 5,336,182 A | 8/1994 | Lundquist et al. | |
| 5,345,938 A | 9/1994 | Nishiki et al. | |
| 5,345,940 A | 9/1994 | Seward et al. | |
| 5,357,550 A | 10/1994 | Asahina et al. | |
| 5,358,478 A | 10/1994 | Thompson et al. | |
| 5,364,351 A | 11/1994 | Heinzelman et al. | |
| 5,385,148 A * | 1/1995 | Lesh et al. | 600/471 |
| 5,385,544 A * | 1/1995 | Edwards et al. | 604/22 |
| 5,395,327 A | 3/1995 | Lundquist et al. | |
| 5,456,258 A | 10/1995 | Kondo et al. | |
| 5,456,664 A | 10/1995 | Heinzelman et al. | |
| 5,469,852 A * | 11/1995 | Nakamura et al. | 600/463 |
| 5,470,350 A | 11/1995 | Buchholtz et al. | |
| 5,499,630 A | 3/1996 | Hiki et al. | |
| 5,531,686 A | 7/1996 | Lundquist et al. | |
| 5,560,362 A | 10/1996 | Sliwa, Jr. et al. | |
| 5,568,815 A * | 10/1996 | Raynes et al. | 600/485 |
| 5,630,837 A * | 5/1997 | Crowley | 601/2 |
| 5,662,116 A | 9/1997 | Kondo et al. | |
| 5,671,738 A * | 9/1997 | Thornberg | 600/407 |
| 5,697,965 A | 12/1997 | Griffin, III | |
| 5,699,805 A | 12/1997 | Seward et al. | |
| 5,704,361 A | 1/1998 | Seward et al. | |
| 5,706,823 A | 1/1998 | Wodlinger | |
| 5,713,363 A | 2/1998 | Seward et al. | |
| 5,715,817 A | 2/1998 | Stevens-Wright et al. | |
| 5,749,364 A | 5/1998 | Sliwa, Jr. et al. | |
| 5,788,636 A | 8/1998 | Curley | |
| 5,795,299 A | 8/1998 | Eaton et al. | |
| 5,797,848 A | 8/1998 | Marian et al. | |
| 5,807,253 A | 9/1998 | Dumoulin et al. | |
| 5,807,324 A | 9/1998 | Griffin, III | |
| 5,843,026 A | 12/1998 | Edwards et al. | |
| 5,846,205 A | 12/1998 | Curley et al. | |
| 5,888,577 A | 3/1999 | Griffin, III et al. | |
| 5,891,088 A | 4/1999 | Thompson et al. | |
| 5,906,579 A | 5/1999 | Vander Salm et al. | |
| 5,921,978 A | 7/1999 | Thompson et al. | |
| 5,928,276 A | 7/1999 | Griffin, III et al. | |
| 5,931,863 A | 8/1999 | Griffin, III et al. | |
| 5,935,102 A | 8/1999 | Bowden et al. | |
| 5,938,616 A | 8/1999 | Eaton et al. | |
| 5,954,654 A | 9/1999 | Eaton et al. | |
| 6,013,072 A | 1/2000 | Winston et al. | |
| 6,033,378 A | 3/2000 | Lundquist et al. | |
| 6,039,693 A | 3/2000 | Seward et al. | |
| 6,085,117 A | 7/2000 | Griffin, III et al. | |
| 6,144,870 A | 11/2000 | Griffin, III | |
| 6,171,248 B1 | 1/2001 | Hossack et al. | |
| 6,173,205 B1 | 1/2001 | Griffin, III et al. | |
| 6,224,556 B1 | 5/2001 | Schwartz et al. | |
| 6,228,028 B1 | 5/2001 | Klein et al. | |
| 6,228,032 B1 | 5/2001 | Eaton et al. | |
| 6,266,551 B1 * | 7/2001 | Osadchy et al. | 600/424 |
| 6,293,943 B1 * | 9/2001 | Panescu et al. | 606/41 |
| 6,306,096 B1 | 10/2001 | Seward et al. | |
| 6,306,097 B1 | 10/2001 | Park et al. | |
| 6,310,828 B1 | 10/2001 | Mumm et al. | |
| 6,360,027 B1 | 3/2002 | Hossack et al. | |
| 6,368,275 B1 | 4/2002 | Sliwa et al. | |
| 6,385,489 B1 | 5/2002 | Griffin, III et al. | |
| 6,398,731 B1 | 6/2002 | Mumm et al. | |
| 6,423,002 B1 | 7/2002 | Hossack | |
| 6,440,488 B2 | 8/2002 | Griffin, III et al. | |
| 6,443,894 B1 | 9/2002 | Sumanaweera et al. | |
| 6,475,148 B1 | 11/2002 | Jackson et al. | |
| 6,475,149 B1 | 11/2002 | Sumanaweera | |
| 6,482,161 B1 | 11/2002 | Sumanaweera et al. | |
| 6,485,455 B1 | 11/2002 | Thompson et al. | |
| 6,491,633 B1 | 12/2002 | Krishnan et al. | |
| 6,503,202 B1 | 1/2003 | Hossack et al. | |
| 6,517,488 B1 | 2/2003 | Hossack | |
| 6,527,717 B1 | 3/2003 | Jackson et al. | |
| 6,532,378 B2 | 3/2003 | Saksena et al. | |
| 6,554,770 B1 | 4/2003 | Sumanaweera et al. | |
| 6,580,948 B2 | 6/2003 | Haupert et al. | |
| 6,589,182 B1 | 7/2003 | Loftman et al. | |
| 6,605,043 B1 | 8/2003 | Dreschel et al. | |
| 6,607,488 B1 | 8/2003 | Jackson et al. | |
| 6,607,528 B1 * | 8/2003 | Quick et al. | 606/45 |
| 6,612,992 B1 | 9/2003 | Hossack et al. | |
| 6,645,147 B1 | 11/2003 | Jackson et al. | |
| 6,648,875 B2 | 11/2003 | Simpson et al. | |
| 6,709,396 B2 | 3/2004 | Flesch et al. | |
| 6,908,434 B1 * | 6/2005 | Jenkins et al. | 600/466 |
| 6,923,768 B2 | 8/2005 | Camus et al. | |
| 2002/0007198 A1 | 1/2002 | Haupert et al. | |
| 2003/0045796 A1 | 3/2003 | Friedman | |
| 2003/0158483 A1 | 8/2003 | Jackson et al. | |
| 2004/0097805 A1 | 5/2004 | Verard et al. | |

OTHER PUBLICATIONS

David J. Sahn, "Phased Arrays for Multiplane Esophageal Echos in Infants", Summary Statement, Diagnostic Radiology Study Section, Jun. 1990.

David J. Sahn, "Instrumentation and Physical Factors Related to Visualization of Stenotic and Regurgitant Jets by Doppler Color Flow Mapping", JACC, Nov. 1988, pp. 1354-1365, vol. 12, No. 5.

David J. Sahn, "Advances in Ultrasound Imaging for Congenital Heart Disease Diagnosis and Management", Pediatric Cardiology, Nov. 26-Dec. 1, 1989, Proceedings of the III World Congress of Pediatric Cardiology, Bangkok.

David J. Sahn et al., "Important Rolesof Transeophageal Color Doppler Flow Mapping Studies(TEE) in Infants with Congenital Heart Disease", Supplement to Journal of the American College of Cardiology, Feb. 1990, vol. 15, No. 2 (Supplement A).

David J. Sahn, "Applications of Color Flow Mapping in Pediatric Cardiology", Cardiology Clinics, May 1989, pp. 255-264, vol. 7, No. 2.

David J. Sahn et al., "Miniaturized High Frequency Phased Array Devices for High Resolution Neonatal and Intraoperative Imaging", Supplement to Journal of the American College of Cardiology, Feb. 1990, vol. 15, No. 2 (Supplement A).

Piero Tortoli et al., "Velocity Magnitude Estimation with Linear Arrays Using Doppler Bandwidth", Ultrasonics, 2001, pp. 157-161, vol. 39.

Lilliam M. Valdes-Cruz et al., "Transvascular Intracardiac Applications of a Miniaturized Phase-Array Ultrasonic Endoscope", Brief Rapid Communication, Mar. 1991, pp. 1023-1027, vol. 83, No. 3.

Lilliam M. Valdes-Cruz et al., "Experimental Animal Investigations of the Potential for New Approaches to Diagnostic Cardiac Imaging in Infants and Small Premature Infants from Intracardiac and Trasesophageal Approaches Using a 20MHz Real Time Ultrasound Imaging Catheter", Supplement to Journal of the American College of Cardiology, Feb. 1989, vol. 13, No. 2 (Supplement A).

P.N.T. Wells, "Velocity, Absorption and Attenuation in Biological Materials", Biomedical Ultrasonics, 1977, pp. 110-144.

* cited by examiner

SAFETY SYSTEMS AND METHODS FOR ENSURING SAFE USE OF INTRA-CARDIAC ULTRASOUND CATHETERS

CORRESPONDING RELATED APPLICATIONS

The present invention is a continuation in part (CIP) of parent application Ser. No. 10/345,806 entitled "ULTRASOUND IMAGING CATHETER ISOLATION SYSTEM WITH TEMPERATURE SENSOR" filed on Jan. 16, 2003, now U.S. Pat. No. 6,908,434, which claims the benefit of U.S. Provisional Patent Application Ser. No. 60/349,060, filed on Jan. 16, 2002. The present application claims the benefit of and priority to these applications, the entire contents of which being incorporated by reference herein in their entirety.

This application is also related to co-pending application Ser. No. 10/997,898, entitled "METHOD AND APPARATUS FOR ISOLATING A CATHETER INTERFACE", filed concurrently herewith. The entire contents of this co-pending application are incorporated by reference herein in its entirety.

BACKGROUND OF THE INVENTION

1. Field of the Invention

The present invention is directed toward improvements in ultrasound catheters and more particularly toward an ultrasound catheter that includes a temperature monitoring system carried at least in part by the catheter for preventing the overheating of the same.

2. Description of the Related Art

Medical imaging technology is used to improve the diagnosis and treatment of medical conditions. Presently available medical imaging technology includes a wide variety of ultrasound, X-ray, nuclear, magnetic resonance imaging (MRI) and other imaging systems.

For some medical imaging technologies, such as those involving intra-body probes (e.g., ultrasound imaging catheters, electrophysiology (EP) catheters, ablation catheters, etc.), particular attention is paid to thermal safety concerns arising from use of electrical devices within a patient's body. By way of example, intra-body ultrasound catheters typically include an ultrasound transducer which converts electrical voltage to sound waves. Used with higher power, such as that used with color Doppler imaging, and for a lengthy period of time, it is possible that the transducer, and hence, catheter tip, may heat up, and such heat may well be above a safe body temperature. While computer software can be used to regulate the amount of power put into the catheter, a software malfunction could result in too much power being delivered. It is, therefore, desirable to have a safety cut-off mechanism or other control to avoid such a problem.

Actual temperature monitoring near the top or tip of the catheter is most desirable, with feedback to the computer, with an automatic warning or shut down based upon some upper pre-determined temperature limit. The safety standard set in the U.S. FDA guidelines is 43° C. although this may vary depending on the environment in which the catheter is being used.

Other problems with the prior art not described above can also be overcome using the teachings of the present invention, as would be readily apparent to one of ordinary skill in the art after reading this disclosure.

SUMMARY OF THE INVENTION

An embodiment of the present invention includes an intra-cardiac ultrasound catheter having an elongated catheter body, comprising an ultrasound transducer carried by the elongated catheter body for use in imaging, a temperature sensor positioned relative to the ultrasound transducer along the elongated catheter body so as to sense a temperature caused by the ultrasound transducer, and a plurality of wires for coupling the ultrasound transducer and the temperature sensor to a cutoff circuit configured to automatically cutoff power to the ultrasound transducer if the temperature sensed by the temperature sensor exceeds a known value.

Another embodiment of the present invention includes a method of limiting a temperature induced in a body by an ultrasound imaging catheter are provided. The method preferably comprises receiving, at an isolation box, an imaging signal from an imaging catheter, receiving, at an isolation box, a signal indicative of a temperature of tissue adjacent to the imaging catheter, removing power to the imaging catheter at the isolation box if the signal indicates the temperature of tissue adjacent to the imaging catheter exceeds a known value, and sending the imaging signal from the catheter to a processor if the signal indicates the temperature of tissue adjacent to the imaging catheter is less than the limit.

Another embodiment of the present invention includes a safety system for ensuring safe use of an intra-cardiac catheter, comprising means for receiving an imaging signal from the intra-cardiac catheter, means for receiving a signal indicative of a temperature of tissue adjacent to the intra-cardiac catheter, and means for removing power to the intra-cardiac catheter at an isolation box if the signal indicates the temperature of tissue adjacent to the intra-cardiac catheter exceeds a known value.

DETAILED DESCRIPTION OF THE EXEMPLARY EMBODIMENTS

Reference will now be made in detail to exemplary embodiments of the present invention. Wherever possible, the same reference numbers will be used throughout the drawings to refer to the same or like parts.

The present invention provides improved electrical isolation for catheters and similar probes that may be inserted in a body, such as the body of a mammal, including a human. Electrical isolation is important because leakage of electrical current may lead to deleterious effects, including cardiac arrhythmia or cardiovascular collapse. Two types of isolation are important. One type, sometimes referred to as "patient sink leakage current," may arise when an external source of voltage, such as 250 volts from an electrical outlet or electrical equipment, passes through the catheter and the patient's body or between one catheter element and another catheter or catheter element within the body. This type of isolation is associated with equipment fault conditions and is addressed in the design of intrabody probe systems (e.g., electrophysiology electrode catheters and ultrasound imaging catheters) to protect the patient from deleterious shocks caused by an electrical fault. A second type of isolation limits leakage currents that may arise under no fault conditions. Long probes containing conductors, such as electrophysiology and ultrasound imaging catheters, may exhibit electric currents induced in the conductors by electromagnetic radiation present in the room. Patient safety requires limiting both types of leakage currents to low (e.g., 20 microamps or less) levels. Generally, fault-type leakage currents may be isolated on a per catheter (or probe) basis, since a single failure presents a significant threat and there is a low likelihood that multiple faults will occur simultaneously. In contrast, no fault leakage isolation must address multiple catheters (or probes), since leakage currents from induced currents in multiple catheters may be additive. Consequently, isolating each catheter provides improved patient safety. Providing such isolation close to the patient so as to reduce the length of electrical conductors on the patient side of the isolation also improves patient safety. Such measures are of particular importance for intracardiac probes.

Figure 1:
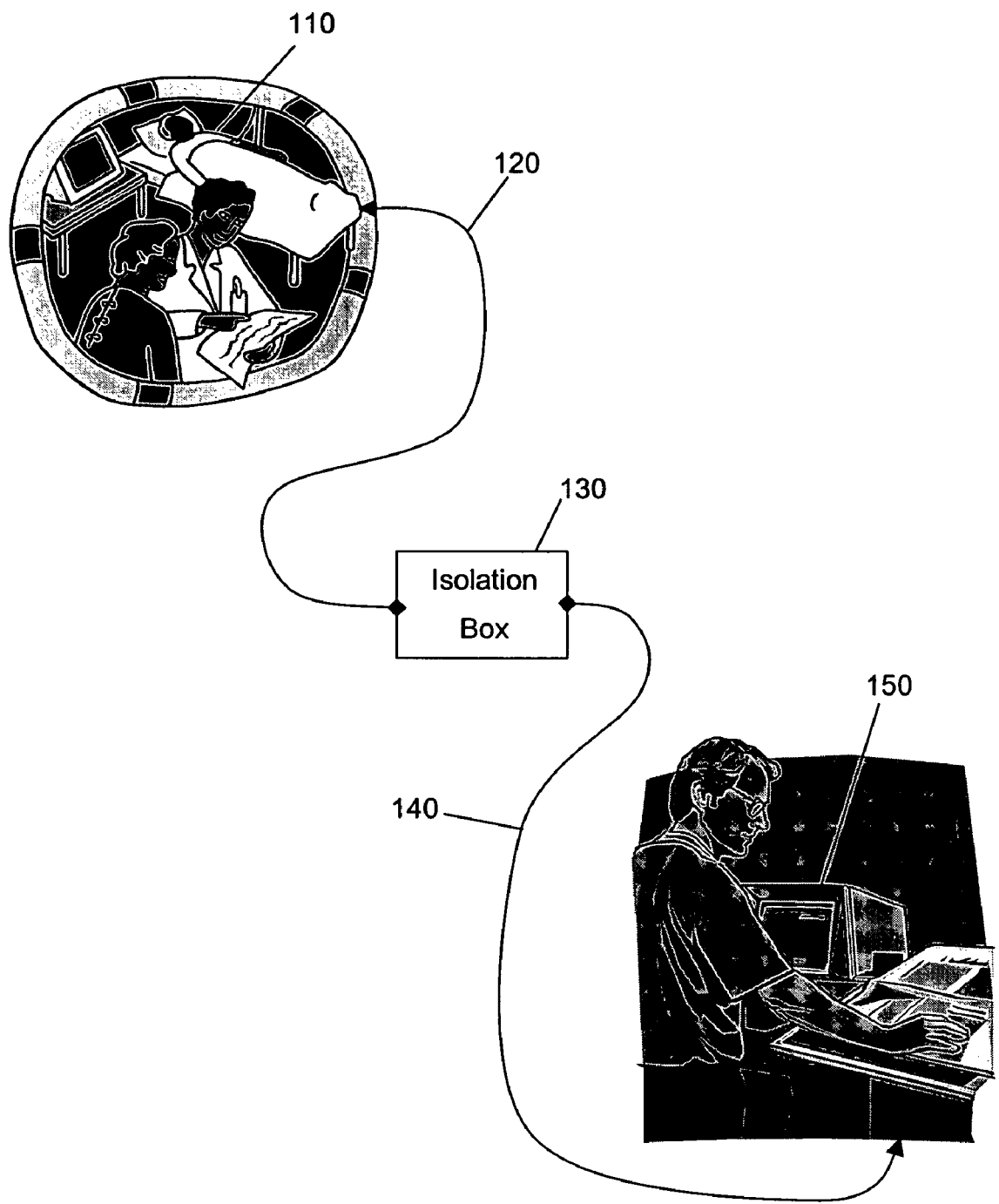
FIG. 1 is a representation of a facility in which a patient undergoes intra-body imaging according to an embodiment of the present invention.

According to an embodiment of the present invention as shown in FIG. 1, an isolation box 130 is provided that electrically couples an imaging probe 120 to an ultrasound equipment 150 via a cable 140. The isolation box 130 is positioned as close to the patient 110 as possible consistent with room layout and sterility limitations (e.g., attached to the patient's bed or operating/imaging table) so as to minimize the length of imaging probe 120.

Figure 2:
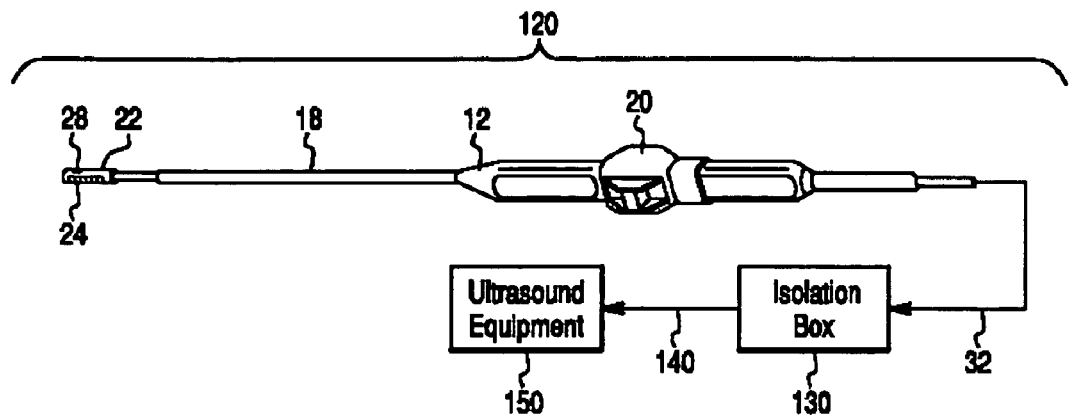
FIG. 2 is a representation of a catheter employing an embodiment of the present invention with an isolation system shown schematically.

The imaging probe 120 preferably includes a catheter and transducer assembly 12 as shown in FIG. 2. In many respects, the catheter and transducer assembly 12 may be constructed in a conventional manner similar, for example, to the ultrasound imaging catheter described in application Ser. No. 09/263,755 filed Mar. 5, 1999, the entire content of said application being incorporated herein by reference. It should be noted that the present invention is not limited to the specific catheter assembly disclosed in the prior referenced application as the invention is applicable to various catheters designed for intravascular/intracardiac echocardiography and for other physiological uses. In particular, the present invention is applicable to any intravascular/intracardiac catheter including an electrical conductor (e.g., a signal or guide wire) that carries electrical currents or in which electrical currents may be induced by electromagnetic radiation.

Figure 3:
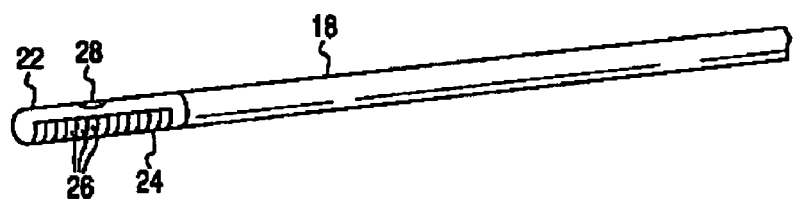
FIG. 3 is a detailed view of an end of the catheter shown in FIG. 2 illustrating an ultrasound transducer and a thermistor.

The catheter assembly 12 includes an elongated catheter generally in the form of a tube 18. The proximal end of the tube 18 is connected to a handle mechanism 20 which could include means for controlling the steering of an ultrasound probe 22 mounted at the distal end of the catheter tube 18. The ultrasound probe 22 includes an ultrasound transducer assembly 24, which is comprised of a number of ultrasonic transducer elements 26 having wires connected thereto which are provided inside the tube. Although only twelve or so transducer elements 26 are shown in FIG. 3, substantially any number of transducer elements may be employed as described in the prior application discussed above. These transducer elements can also be deployed in many geometrical orientations, such as linear, circular, curved, etc. Typically, the transducer includes sixty-four elements.

Mounted near the distal end, such as on the reverse side of the ultrasound transducer probe 22 is a thermistor 28. The thermistor 28 is preferably embedded within the probe 22 so as to provide a smooth outer surface on the probe 22. The exact location of the thermistor 28 is not critical. However, it must be in such a position so as to be able to sense the temperature of the tissue in the vicinity of the probe 22 and/or the temperature of the probe 22 itself without interfering with the operation of the same. Furthermore, while the invention has been described with specific reference to a thermistor 28, it should be readily apparent that other types of safety-related sensors may also be employed which are capable of sensing temperature or other safety-related parameters. The electrical wires leading from the thermistor 28 pass through the inside of the catheter body 18 to the exterior of the body in substantially the same manner as the numerous wires connected to the ultrasonic transducer elements 26.

The ultrasonic equipment 150 illustrated in FIG. 1 is a conventional ultrasound machine which may operate in a manner well known in the art. This equipment 150 may be located a distance from a patient's bed outside of the sterile area. The isolation box 130, however, is intended to be placed on or near a patient's bed within the sterile area, with cable 140 connecting the two together. Alternatively, the isolation box 130 may be placed at the boundary of the sterile area as described more fully below.

The cable 32 from the catheter assembly 12 carries a plug at the end thereof that plugs into the isolation box 130 to form the various electrical connections. Since the isolation box 130 is relatively small and is located on or near the patient's bed, the cable 32 can also be relatively short, thereby reducing the cost of the same. The cable 32 carries all of the leads from the ultrasonic transducers 26, the leads from the thermistor 28 and any other leads that may be used in connection with the catheter assembly 12. For example, the catheter assembly 12 may carry other electrodes and/or transducers at or near the tip thereof or elsewhere along the catheter body 18 for various other purposes.

The isolation box 130 preferably has an input connector or socket 34 for connection to the cable 32 and an output socket or connector 36 for connection to the cable 140 that leads to the ultrasound equipment 150. These may be the card connector disclosed herein or conventional sockets or connectors well known in the art.

Figure 4:
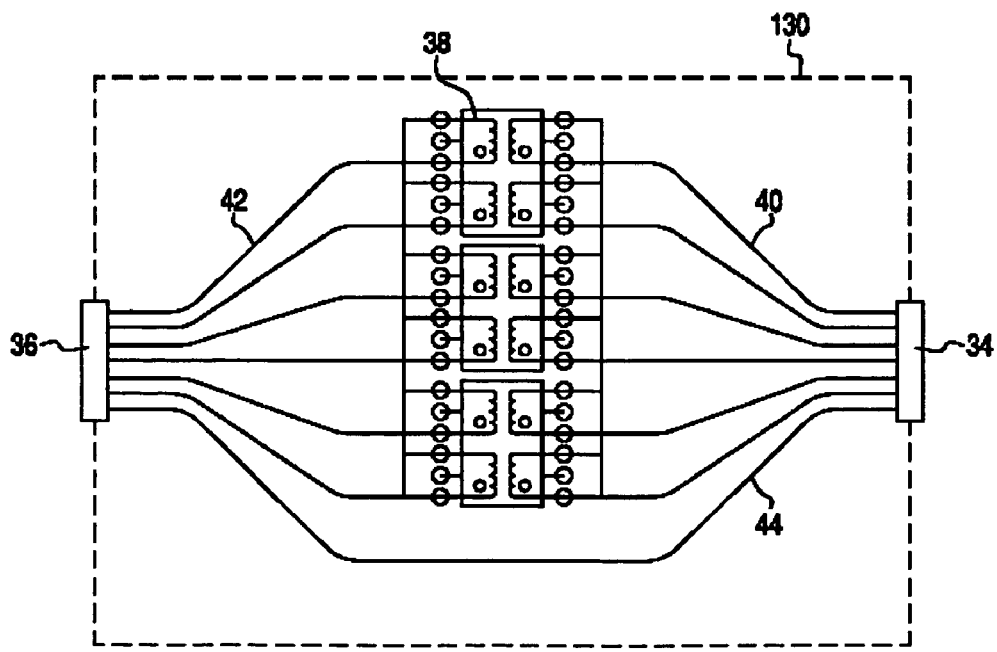
FIG. 4 is a schematic representation of an isolation circuit according to an embodiment of the present invention.

According to an embodiment of the present invention, the isolation box 130 includes a plurality of isolation transformers 38 as shown in FIG. 4. In order to keep the isolation box 130 as small as possible, relatively small transformers 38 are utilized as a significant number of them are typically implemented within the isolation box 130. There may be one isolation transformer 38 for each of the ultrasonic transducer elements 26 and, potentially, an opto isolator for the thermistor 28. Thus, if there are sixty-four transducer elements 26, an equal number (i.e., sixty-four transformers) of transformers 38 are required. One transformer which may be used with various embodiments of the present invention is a wide band isolation transformer sold by Rhombus Industries Inc. of Huntington, Calif. as Rhombus Model No. T-1113.

One side of each transformer 38 may be connected by leads 40 to the socket or connector 34 so as to be connected to the transducer assembly 12 by way of the cable 32. Similar leads 42 connect the opposite side of each transformer 38 to the socket or connector 36 for ultimate connection to the ultrasound equipment 150 through the cable 140. Other leads such as shown at 44 may pass directly through the isolation box 130 from connector 34 to connector 36 without being connected to an isolation transformer 38 if the same is desired. For example, the lead from the thermistor 28 may or may not pass through an isolation transformer 38 but may be connected directly to the ultrasound equipment 150 by passing through the isolation box 130. Alternative isolation circuitry may also be employed. As should be readily apparent to those skilled in the art, appropriate circuitry may be located either in the isolation box 130 or the ultrasound equipment 150 or elsewhere for interpreting the signal from the thermistor 28 for controlling the ultrasound equipment 150 in response thereto.

Figure 5:
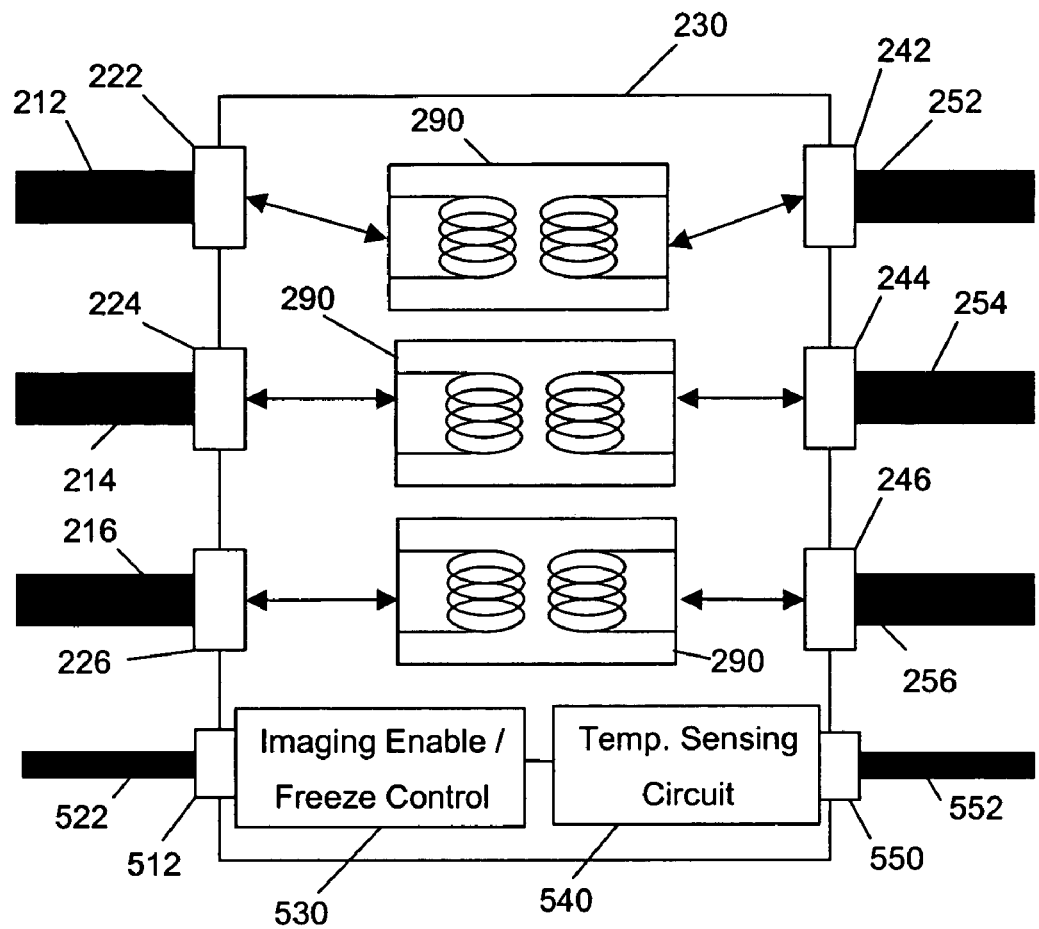
FIG. 5 is a schematic representation of an isolation box according to an embodiment of the present invention.

An isolation box 230 according to an embodiment of the present invention is shown in the block diagram of FIG. 5. According to this embodiment, the isolation box 230 includes a plurality of probe ports 222, 224, 226 for coupling to a plurality of probe elements 212, 214, 216 respectively. While only three probe ports 222, 224, 226 and three probe elements 212, 214, 216 are shown, the number of ports and probes, and the types of ports and probes may vary for any given implementation. By way of example, the isolation box 230 may include sixty-four or more edge contact connector type ports for sixty-four individual probe elements. Further, the same isolation box 230 might also include one or more other connectors that pertain to other elements, such as an EP recording system, a mapping system, etc., as shown in the exemplary implementation of FIG. 7.

Figure 7:
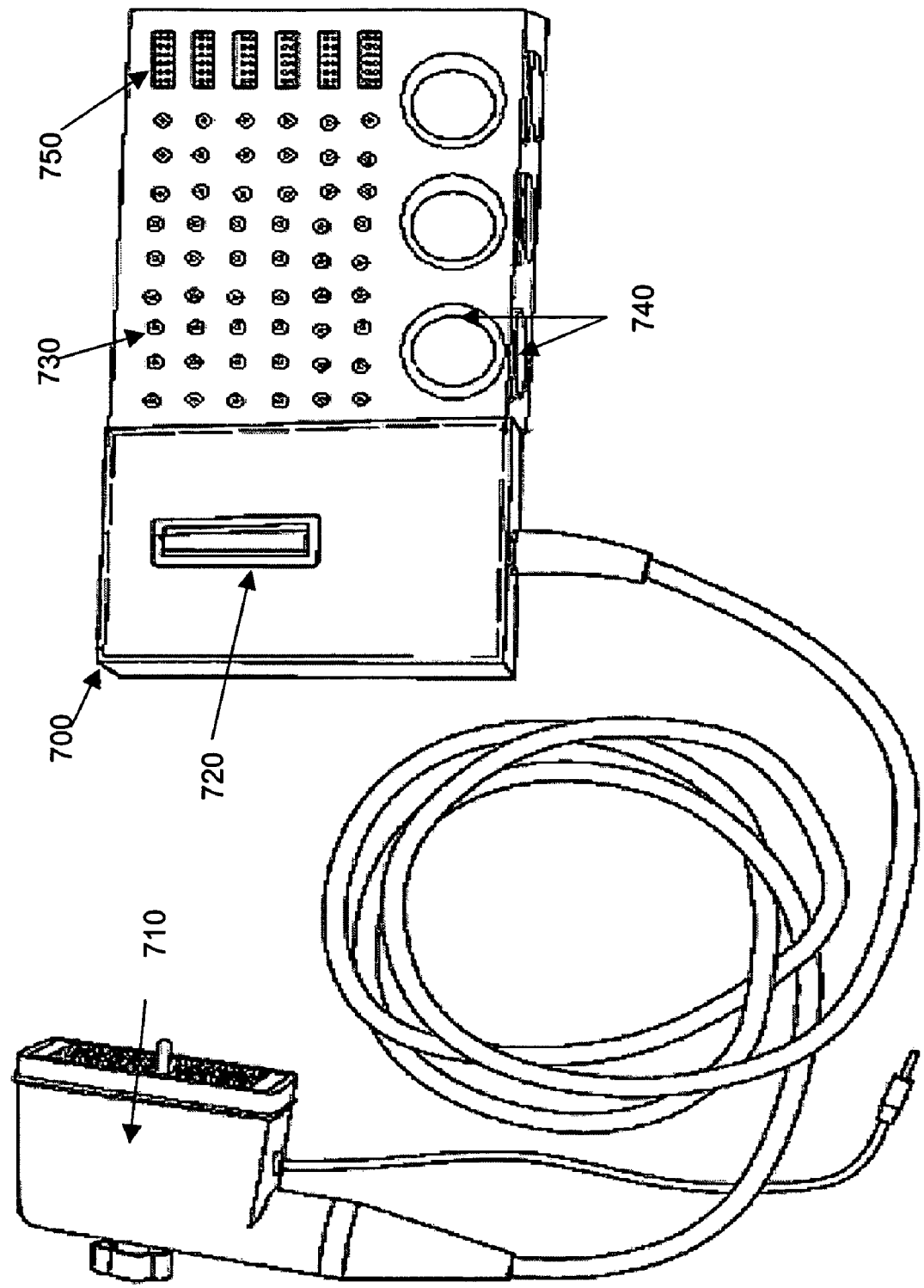
FIG. 7 is a perspective view of an isolation box according to an embodiment of the present invention.

The probe ports 222, 224, 226 are coupled to one or more processor ports 242, 244, 246 (after passing through isolation circuit 290) for coupling to a corresponding number of processor cables 252, 254, 256. According to one embodiment of the present invention, the processor ports are integrated into a one or more high-density ZIF connector(s) 710 as shown in FIG. 7. The integrated port 710 may be coupled to one or more processors via one or more high-density cables. Other configurations are also contemplated.

Additionally, one ore more of ports 242, 244, 246 and/or 710 may be configured to have a card connector pass through a plastic barrier to establish an electrical connection therewith. In this manner, the plastic barrier serves as a boundary between the sterile and non-sterile environments, and may be disposable to allow re-use of one or more of the various components. The plastic barrier may comprise, for example, a plastic sleeve/bag, etc.

According to an embodiment of the present invention, filter(s) may be included in the isolation box to suppress noise on an imaging signal from a probe of a first type caused by a probe of a second type. As an example, a bandpass filter may be employed in-line with an ultrasound imaging probe element to suppress noise generated by a radio-frequency (RF) probe. By providing signal filtering such as band limiting filters, the isolation box provides greater capacity for multiple probes of differing types to operate at the same time. Similarly, stages of amplification and impedance matching circuits could also be deployed to enhance signal-to-noise ratios of various signals passed through such an isolation mechanism.

Additionally, according to an embodiment of the present invention, the thermistor 28 automatically shuts off the catheter assembly 12 at the isolation box 130. By way of example, an output of thermistor 28 may be coupled to an enable/disable input to a plurality of gates gating wires passing to/from the transducer elements 26. So long as the temperature of catheter assembly 12 remains at a safe level, such as not more than about 43° C., the gates remain enabled allowing signals to pass to/from transducer elements 26. However, should the temperature of catheter assembly 12 reach or exceed an unsafe level, thermistor 28 disables the gates, automatically shutting off the catheter assembly 12. Other configurations for automatic shutoff are also contemplated.

Figure 6:
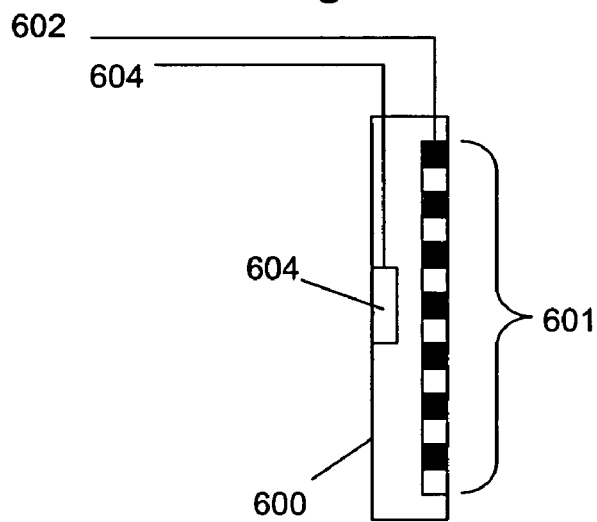
FIG. 6 is a schematic view of linear phased array transducer with a thermistor according to an embodiment of the present invention.

One such scenario would be to provide a thermistor 604 behind a linear ultrasound transducer array 601 (forming part of probe 120), as shown in FIG. 6, coupled via wires 602, 604 to the isolation box 230 shown in FIG. 5. Preferably, the wire 604 is coupled to port 550 on isolation box 230. Additionally, the isolation box 230 includes port 512 coupled to ultrasound equipment 150 via wire 522. The isolation box 230 is configured to disable transmission of ultrasound signals from the ultrasound equipment 150 by disabling the transmit circuitry by signaling the ultrasound equipment 150 through a trigger mechanism such as a hardware interrupt. In particular, the isolation box 230 may include a temperature sensing circuit 540 for sensing a temperature of transducer array 601 via thermistor 604, and an imaging enable/freeze control circuit 530 for disabling the transmit circuitry based on the temperature sensed by temperature sensing circuit 540. Other mechanisms could include disabling an array of multiplexers or transmit channel amplifiers commonly used in such circuits.

An example of an ultrasound catheter connector and isolation system employing an embodiment of the present invention is shown in FIG. 7. In particular, the system includes a patient side isolation module 700 (preferably with thermal cutoff circuitry), with a plurality of interconnection ports for coupling with various electrical components. In particular, the system preferably includes a ZIF connector 710, a plurality of catheter ports 730, 750, a plurality of position management ports 740, and a card edge connector 720. The ZIF connector 710 may be provided for coupling with ultrasound equipment 150. The plurality of catheter ports 730, 750 may be provided for coupling with intra-body catheters (e.g., ultrasound imaging catheters, electrophysiology catheters, etc.). The plurality of position management ports 740 may be provided for coupling with positioning catheters. Other configurations are also contemplated.

The aforementioned system provides the user with a relatively small, and compact device which can be positioned close to the patient, and is relatively easy to sterilize. Thus, the system is easier to use, safer for the patient, and has a lower maintenance cost due to a reduction in the amount of single use cabling. Other advantages and features will be readily apparent to those of skill in the art after reading this disclosure.

The foregoing description of various embodiments of the invention has been presented for purposes of illustration and description. It is not intended to be exhaustive or to limit the invention to the precise form disclosed, and modifications and variations are possible in light of the above teachings or may be acquired from practice of the invention. By way of example, the present invention is applicable to any catheter-instrument, such as lasers, optical imagers, thermal ablation devices, RF ablation devices, and ultrasound ablation devices in addition to the devices described above. The embodiments were chosen and described in order to explain the principles of the invention and its practical application to enable one skilled in the art to utilize the invention in various embodiments and with various modifications as are suited to the particular use contemplated.

What is claimed is:

1. An intra-cardiac ultrasound imaging catheter system, comprising:
an intra-cardiac ultrasound imaging catheter having an elongated catheter body, the catheter including:
an imaging ultrasound transducer carried by the elongated catheter body, the ultrasound transducer configured to generate and receive ultrasound energy;

a temperature sensor positioned relative to the imaging ultrasound transducer along the elongated catheter body so as to sense a temperature caused by the ultrasound transducer; and a plurality of wires for coupling to the imaging ultrasound transducer and the temperature sensor;

a separate isolation box electrically coupled to the plurality of wires and to a cable; and ultrasound equipment coupled to the cable, wherein the isolation box includes a cutoff circuit comprising an enable/disable input to a plurality of gates, the enable/disable input configured to receive signals from the temperature sensor and automatically cut off power to the ultrasound transducer from the ultrasound equipment by gating wires in the isolation box leading to the plurality of wires for coupling to the transducer elements if the temperature sensed by the temperature sensor exceeds a known value.

2. The intra-cardiac ultrasound imaging catheter system as claimed in claim 1, wherein said temperature sensor comprises a thermistor.

3. The intra-cardiac ultrasound imaging catheter system as claimed in claim 1, wherein said ultrasound transducer comprises a plurality of transducer elements.

4. The intra-cardiac ultrasound imaging catheter system as claimed in claim 3, wherein said cutoff circuit comprises an isolation circuit including a plurality of transformers.

5. The intra-cardiac ultrasound imaging catheter system as claimed in claim 4, wherein the number of transformers is equal to the number of transducer elements.

6. The intra-cardiac ultrasound imaging catheter system as claimed in claim 1, wherein the known value is about 43° C.

7. The intra-cardiac ultrasound imaging catheter system as claimed in claim 1, wherein the gates are configured to allow signals to pass to/from the transducer while the temperature sensed by the temperature sensor is less than about 43° C. and to shut off signals to the transducer when the temperature sensed by the temperature sensor exceeds about 43° C.

8. A method of limiting a temperature induced in a body by an ultrasound imaging catheter, comprising:

receiving, at an isolation box that is separate from ultrasound equipment or an ultrasound imaging catheter, an imaging signal from the ultrasound imaging catheter;

receiving, at an enable/disable input to a plurality of gates in the isolation box, a signal indicative of a temperature of tissue adjacent to the ultrasound imaging catheter;

automatically removing power to the ultrasound imaging catheter at the isolation box by gating wires in the isolation box coupling power to the ultrasound imaging catheter if the signal indicates the temperature of tissue adjacent to the ultrasound imaging catheter exceeds a safe level; and automatically allowing the imaging signal from the catheter to pass to ultrasound equipment if the signal indicates the temperature of tissue adjacent to the ultrasound imaging catheter is less than the safe level.

9. The method as claimed in claim 8, wherein the signal indicative of a temperature of tissue adjacent to the ultrasound imaging catheter is generated by a thermistor.

10. The method as claimed in claim 8, wherein the safe level is about 43° C.

11. An isolation box for ensuring safe use of a separate intra-cardiac ultrasound imaging catheter, comprising:

means for receiving an imaging signal from the intra-cardiac ultrasound imaging catheter;

means for receiving a signal indicative of a temperature of tissue adjacent to the intra-cardiac ultrasound imaging catheter at an enable/disable input;

means for automatically removing power to the intra-cardiac ultrasound imaging catheter at the isolation box if the signal indicates the temperature of tissue adjacent to the intra-cardiac ultrasound imaging catheter exceeds a known value comprising a plurality of gates in the isolation box coupling power to the separate intra-cardiac ultrasound imaging catheter when the temperature of tissue adjacent to the intra-cardiac ultrasound imaging catheter is less than the known value; and means for connecting the isolation box to a separate ultrasound equipment.

12. The isolation box as claimed in claim 11, wherein the intra-cardiac ultrasound imaging catheter includes means for generating an ultrasound imaging signal.

13. The isolation box as claimed in claim 11, further comprising means for isolating electrical currents propagating along the intra-cardiac ultrasound imaging catheter.

14. The isolation box as claimed in claim 11, wherein the known value is about 43° C.

* * * * *